United States Patent [19]

Rosa

[11] Patent Number: 5,013,322
[45] Date of Patent: May 7, 1991

[54] YAG COMPATIBLE POSTERIOR CHAMBER INTRAOCULAR IMPLANT

[76] Inventor: Daniele S. A. Rosa, 28, Avenue Raphael, 75016 Paris, France

[21] Appl. No.: 800,719

[22] Filed: Nov. 22, 1985

[51] Int. Cl.$^5$ .............................................. A61F 2/16
[52] U.S. Cl. ............................................................ 623/6
[58] Field of Search ................................................ 623/6

[56] References Cited

U.S. PATENT DOCUMENTS

| | | | |
|---|---|---|---|
| 4,418,431 | 12/1983 | Feaster | 623/6 |
| 4,476,591 | 10/1984 | Arnott | 623/6 |
| 4,485,499 | 12/1984 | Castleman | 623/6 |
| 4,648,879 | 3/1987 | Kelman | 623/6 |

OTHER PUBLICATIONS

Lens Styles from Cilco (Advertisement Brochure) SK-4 Posterior Chamber Lens (Style SK-4), Oct. 1982.
Surgery News-An Advertising supplement, Aug. 1, 1985, vol. 3, No. 15, Clayman Ovoid Model No. 8743 and Kratz/Johnson 7 mm Lightweight Model No. 8663, (2 pages).
"The Jaffe Single Piece Posterior Chamber Lens from Cilco" Advertisement Brochure from Cilco, Oct. 1984, 2 pages.

*Primary Examiner*—Ronald Frinks
*Attorney, Agent, or Firm*—Eckert Seamans Cherin & Mellott

[57] ABSTRACT

A posterior chamber ocular implant compatible with treating secondary cataracts by means of a YAG laser beam. A lens (1) has two convex faces (1a, 1b) and spacer members (10) for spacing the posterior capsule away from the posterior face (1b) of the lens. The spacer members project from the bases (11) of the haptics (2) used for fixing the lens in the eye. The lens makes it possible to treat possible secondary cataracts using a YAG laser without running the danger of marking the implant.

2 Claims, 2 Drawing Sheets

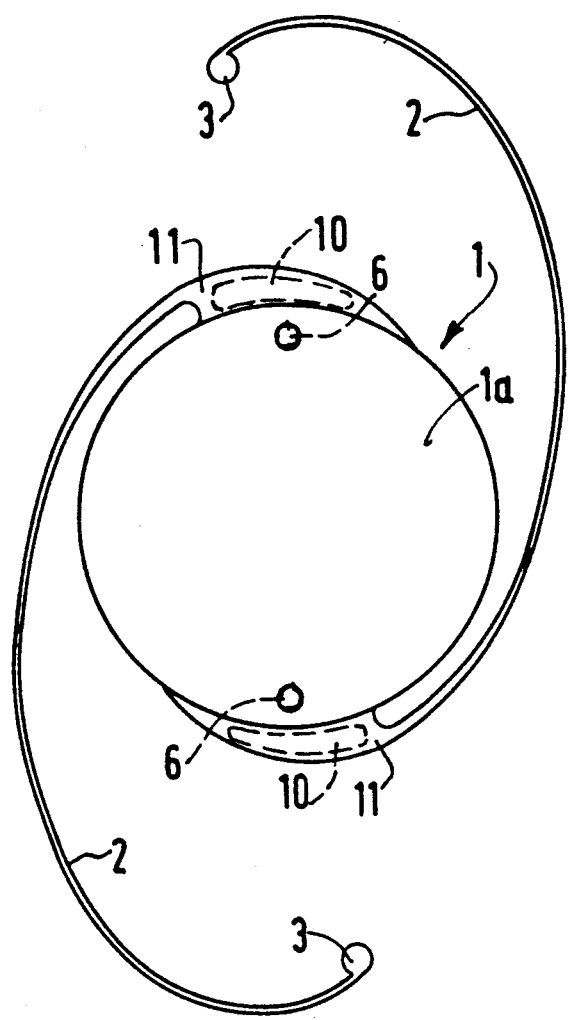
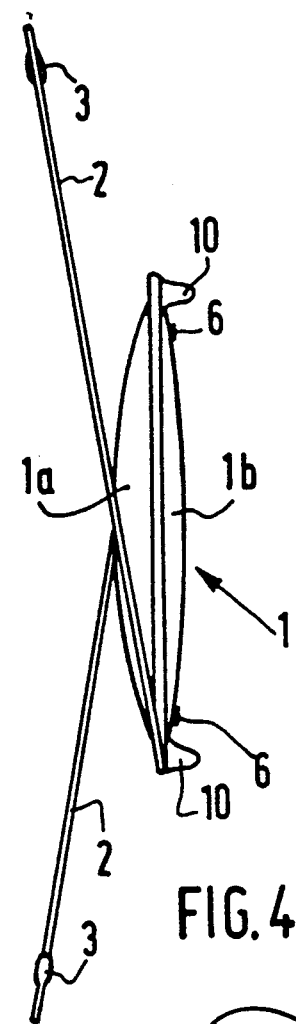
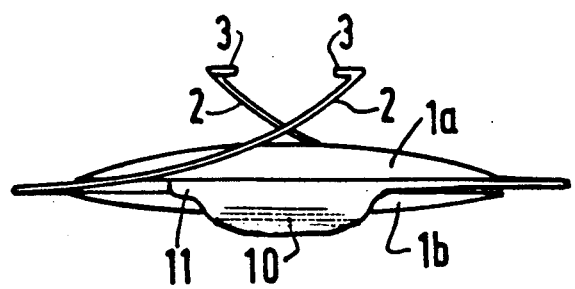
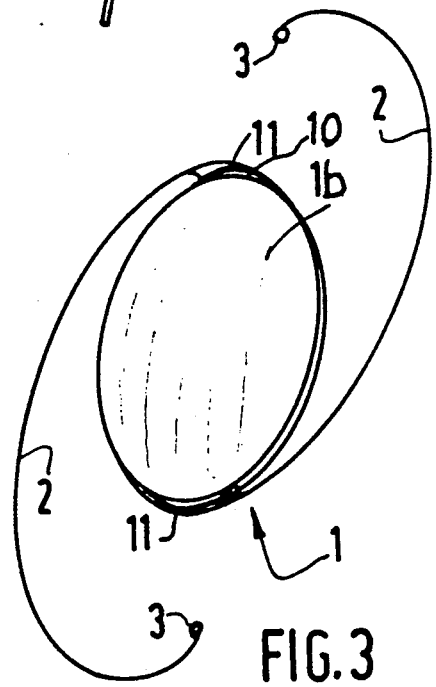
FIG.1
FIG.2
FIG.3
FIG.4

YAG COMPATIBLE POSTERIOR CHAMBER INTRAOCULAR IMPLANT

The present invention relates to an intraocular implant or artificial lens for the posterior chamber and suitable for being implanted in the eye after a cataract operation. The implant is additionally suitable for enabling a subsequent operation to be performed using a YAG laser should a secondary cataract appear. The purpose of implanting an artificial lens is to make it possible for the patient to see without having to wear very thick eyeglasses (10 or 12 diopters) in order to overcome the complete absence of any lens in the eye.

BACKGROUND OF THE INVENTION

The natural lens in the human eye is a transparent structure having a diameter of about 9 mm and a thickness of about 5 mm. It is generally lentil-shaped and is suspended behind the iris by zonular fibers which connect the lens to the ciliary body. A cataract is an opaque portion of the lens or of the anterior or posterior capsules which constitute a lens-enclosing bag. A cataract operation consists in removing the lens, and is designated as being an "intracapsular" operation when the capsule is removed together with the lens, and as being an "extracapsular" when the anterior capsule is removed together with the lens while the posterior capsule is left in place inside the eye.

The first intraocular lens was implanted by Ridley in 1949, and since then, various different types of artificial lens have been proposed. Particular mention may be made of U.S. Pat. Nos. 3,991,426 and 4,092,743.

One of the most critical problems with implanting and wearing an intraocular lens is the problem of fixing the implant inside the ocular cavity. For reasons of tolerance, instead of implanting lenses in the iris plane, lenses are now implanted either in the anterior chamber constituted by the cornea and the iris, or else in the posterior chamber constituted by the iris and the posterior lens capsule which is situated in front of the hyaloid membrane of the vitreous body.

In order to allow for a possible subsequent operation on a secondary cataract, proposals have been made in U.S. Pat. No. 4,244,860 to provide an annular lip including an opening on the posterior face of the optical part of an implant. It is thus possible, albeit difficult, to pass a sharp instrument through the opening to open the opaque posterior capsule without removing the implant. Unfortunately, the posterior capsule tends to invaginate itself inside the annulus against the posterior face of the implant.

Also, the Applicant has developed a new therapy using a pulsed laser beam emitted by a YAG rod operating in locked mode and operating by optical puncturing inside accurately determined regions of the eye without needing to open the eye (U.S. Pat. No. 4,309,998). It is thus possible using the apparatus described in that patent specification to open an opaque lens envelope in a fraction of a second without needing to use conventional ophthalmological surgical instruments, i.e. without opening the eye. Unfortunately, laser treatment performed behind an artificial lens may mark the lens. Since the capsule bears against the posterior face of the implant, there is a danger of the implant being permanently marked by the laser beam which is used to open the capsule.

The Applicant has already described, in U.S. patent application Ser. No. 540,796, an implant for mitigating this drawback by holding the posterior capsule away from the plane posterior face of the lens. In order to avoid the possibility of future laser marking on such an implant, the rear face of the lens is provided with spacer members serving to hold the posterior capsule away from the rear face of the lens by a distance of not less than 0.3 mm. Moreover, a particular biconvexity of the optics empeaches the YAG laser beam to be converged inside the body of the lens or at its posterior surface because as described in the U.S. Pat. No. 4,309,998 the true safety YAG implant distance is from 0.5 mm up to 1 mm and no spacers will provide this space without damaging the iris.

However, in some cases, it turns out that patients fitted with such implants can see the internal portions of the spacer members and they find this is disagreeable.

An object of the present invention is to mitigate this drawback.

Another object of the present invention is to provide an implant which ensures that adequate tension is applied to the posterior capsule.

Yet another object of the present invention is to provide an implant which makes it possible to operate completely safely on a secondary cataract.

SUMMARY OF THE INVENTION

According to the present invention, a posterior chamber intraocular implant comprising a lens of circular section, haptics for fixing the lens inside the bag or the ciliary sulcus, and spacer members for spacing the posterior capsule away from the lens includes the improvement whereby said spacer members are disposed on the bases of the haptics.

Thus, the visual field is completely clear. Further, the posterior capsule is stretched at its extremities so that the entire surface of the capsule is kept taut in a uniform manner.

The lens is preferably a biconvex lens, with the radius of curvature of the posterior face being substantially 3.5 times the radius of curvature of the anterior face.

In this manner, the lens does not modify the geometry of a YAG laser beam, other than to cause the point of focus of the infrared YAG beam to be offset from the point of focus of the red aiming laser which is generally of the helium-neon type. Aiming error is not a problem since the offset is away from the lens surface, i.e. any error is on the safe side.

The implant (i.e. the lens, the haptics, and the spacer members) is preferably constituted as a single piece. This piece is advantageously made from polypropylene polymethyl methacrylate (PMMA) or "Perspex" (Registered Trademark) by shaping on a lathe or by molding. Although these materials give rise to a "hard" lens, it will be understood that the invention is also applicable to materials which give rise to so-called "soft" lenses such as HEMA, Hydrogels... The lens diamater preferably lies in the range 6.1 to 7 mm.

BRIEF DESCRIPTION OF THE DRAWINGS

Embodiments of the invention are described by way of example with reference to the accompanying drawings, in which:

FIGS. 1 to 4 show a first YAG compatible implant seen from in front, from above, in perspective, and from one side, respectively;

DESCRIPTION OF THE PREFERRED EMBODIMENT

Figure 5:
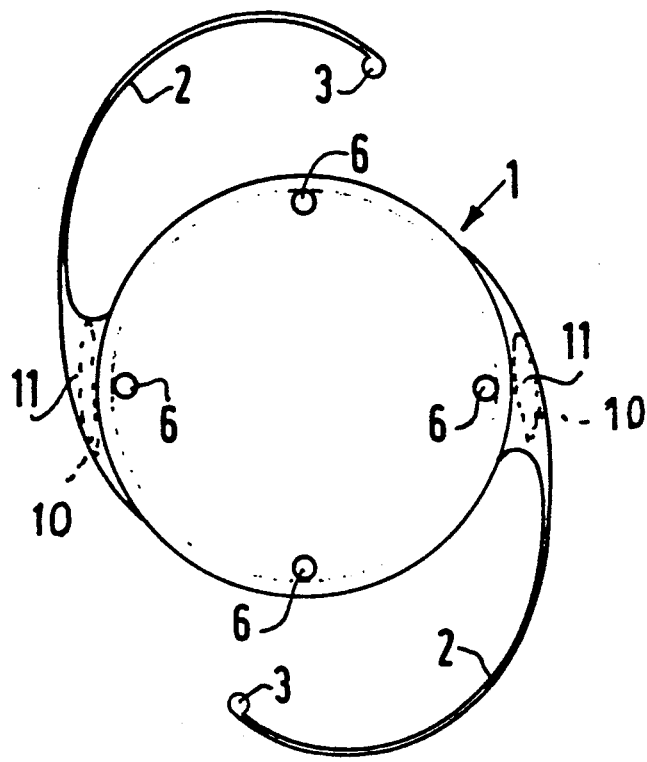
FIG. 5 is a front view of a second embodiment.

In the examples shown, the implant 1 comprises a biconvex lens whose front face 1a is considerably more convex than its rear face 1b which has a radius of curvature which is substantially equal to 3.5 times the radius of curvature of the front face 1a. Naturally, the radius of curvature of the front face depends on the correction it is intended to provide.

The more convex front face 1a of the implant 1 and the less convex rear face 1b can clearly be seen in FIGS. 1 to 4, as can the loops or haptics 2 which are advantageously terminated by rounded olive-shaped ends 3 to avoid damaging the ciliary body. The loops 2 are "Sinskey" style loops and they are inclined at an angle of 10° to the median plane of the lens. In a manner known per se, the lens 1 has at least two diametrically opposed positioning holes 6 which define the 6 o'clock and 12 o'clock positions and which have a diameter of between 0.2 mm and 0.4 mm.

The diameter of the lens 1 is preferably in the range 6.1 mm to 7 mm. Given the presence of the spacer members, it has been observed that conventional lenses tend to slide over the capsule and be a nuisance to the person in which they are implanted. It is very difficult to implant lenses having a diameter of more than 7 mm because of the difficulty of inserting them into the bag.

In accordance with the invention, and as can be seen in FIGS. 1 to 4, the haptics 2 are fixed to the periphery of the lens by base 11 from which they extend tangentially so that their ends are located substantially on the vertical axis of the lens after following a looping path. Projections 10 are formed on the bases 11 on the same side as the face 1b and the extremities of the projections which come into contact with the posterior capsule are rounded in shape (see FIG. 2) so as to be substantially in the shape of an arc of a circle. The sides of the spacer members 10 are tangential to the sides of the bases 11 in such a manner as to avoid any sharp angles in the vicinity of the posterior capsule. The maximum height of the spacer members 10 above the edge of the lens 1 is about 0.5 mm so that in the middle of the lens the distance between the capsule and the face 1b is about 0.3 mm. In this first embodiment of the invention, the bases 11 of the loops are disposed close to the 6 o'clock and 12 o'clock holes.

Figure 6:
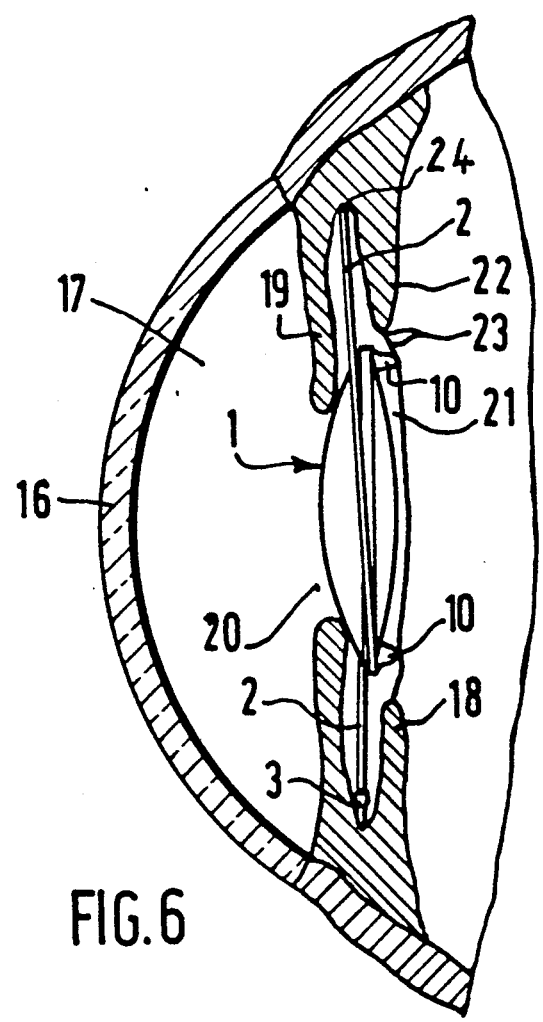
FIG. 6 is a side view of an implant in accordance with the invention and in position in the eye.

In a second embodiment, shown in FIG. 5, there are four positioning holes 6, the loops are shorter, and their bases 11 are disposed close to the 3 o'clock and 9 o'clock holes. Naturally, some other number of haptics may be provided, e.g. 3, in which case they would be at regular intervals of 120°. FIG. 6 shows an implant in accordance with the invention in position inside an eye. This figure shows the transparent cornea 16, the anterior chamber 17, the pupil 20 in the middle of the iris 19, the posterior capsule 21 which is connected to the extension of the ciliary body 22 by zonular fibers 23. The loops 2 rest against the ciliary body 24.

As can be seen in FIG. 6, the posterior capsule 21 is stretched over the spacer members 10 and this has the effect of delaying the appearance of secondary cataracts therein.

Naturally numerous variants may be applied to the invention without going beyond its scope as defined by the accompanying claims, i.e. if the lens is made of a soft material, the loops should be thicker and longer to provide stability inside the bag.

I claim:

1. A YAG compatible posterior chamber intraocular implant, comprising a biconvex lens of circular section, the lens having a posterior face with a radius of curvature which is substantially equal to 3.5 times a radius of curvature of the anterior face, haptics for fixing the implant inside the natural lens bag or the ciliary sulcus, the haptics being affixed to the periphery of the lens by bases, the bases being arcuate in configuration and being tangentially positioned relative to the lens, the haptics extending tangentially from the bases, and spacer members for spacing the posterior capsule from the lens, the said spacer members being disposed on the bases of the haptics, the sides of the spacer members being tangential to the sides of the bases, the height of the spacer members above the edge of the lens being about 0.5 mm.

2. A YAG-compatible posterior chamber intraocular implant comprising a biconvex lens of circular section, the lens having a posterior face with a radius of curvature which is substantially equal to 3.5 times a radius of curvature of the anterior face, at least two haptics for fixing the implant inside the natural lens bag or the ciliary sulcus on the periphery of which are tapered at least two base elements for the haptics wherein on the rear face of the implant are provided discontinuous spacer members for spacing the posterior capsule of the eye from the lens, said spacer members being disposed on said bases of the haptics, and being rounded and projecting about 0.5 mm from the posterior faces of the bases of the haptics.

* * * * *